United States Patent [19]

Tournayre et al.

[11] 4,025,554

[45] May 24, 1977

[54] HALOGENO-ACETANILIDES AS HERBICIDES

[75] Inventors: Jean Claude Tournayre, Basel; Christian Vogel, Binningen, both of Switzerland

[73] Assignee: Ciba-Geigy Corporation, Ardsley, N.Y.

[22] Filed: Aug. 28, 1972

[21] Appl. No.: 284,203

[30] Foreign Application Priority Data

Sept. 1, 1971 Switzerland ............... 12818/71

[52] U.S. Cl. ..................... 260/562 A; 71/118
[51] Int. Cl.² ........................... C07C 10/10
[58] Field of Search ......... 260/562, 562 A; 71/118

[56] References Cited

UNITED STATES PATENTS

| 3,268,324 | 8/1966 | Hamm et al. ............. 260/562 |
| 3,442,945 | 5/1969 | Olin ............................ 260/562 |

FOREIGN PATENTS OR APPLICATIONS 1,419,116 10/1965 France ..................... 260/562

*Primary Examiner*—John D. Randolph
*Attorney, Agent, or Firm*—Harry Falber

[57] ABSTRACT

N-(Cycloalkylalkoxymethyl)-halogenoacetanilides are very suitable for selectively combating of weeds in cultivated plants such, for example, as maize, soya, cotton, sorghum sugar beets.

12 Claims, No Drawings

HALOGENO-ACETANILIDES AS HERBICIDES

The present invention relates to substituted halogeno-acetanilides, a process for their manufacture, also to herbicidal agents which contain these new compounds in the form of active substances, and to processes for selectively combating weeds in crops of cultivated plants, which comprise the use of the active substances or of agents which contain them.

The new substituted halogeno-acetanilides correspond to the formula I

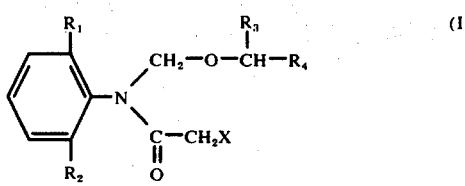

wherein $R_1$ and $R_2$ each independently represents hydrogen or lower alkyl containing from 1 to 4 carbon atoms, $R_3$ represents hydrogen or the methyl group, $R_4$ represents cycloalkyl containing from 3 to 5 carbon atoms, and X represents chlorine or bromine.

By lower alkyl radicals $R_1$ and $R_2$ containing from 1 to 4 carbon atoms are meant the methyl, ethyl, n-propyl, isopropyl, n-butyl, isobutyl, sec. or tert.butyl radicals. Suitable cycloalkyl radicals are the cyclopropyl, cyclobutyl or cyclopentyl radicals; the cyclopropyl radical is preferred.

The new substituted halogeno-acetoanilides of the formula I are obtained according to the invention by converting a halogeno-acetyl halide of the formula II $$Hal - CO - CH_2X \qquad (II)$$

with a phenylazomethine of the formula III

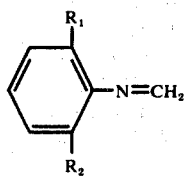

into a halogeno-acetanilide, and reacting this latter with an alkanol of the formula IV

R_4—CH—OH (IV)

in the presence of an acid binding agent.

The symbols $R_1$, $R_2$, $R_3$, $R_4$ and X in the formulae II-IV have the meanings given under the formula I. In a formula II, Hal represents halogen, preferring chlorine or bromine.

The reactions are carried out in the presence of solvents or diluents which are inert towards the reactants. The following, for example, may be used: aliphatic, aromatic or halogenated hydrocarbons, such as benzene, toluene, xylene, hexane, heptane, petroleum ether, chlorobenzene, methylene chloride, ethylene chloride, chloroform; ether and ethereal compounds, such as dialkyl ether, dioxan, tetrahydrofuran; ketones, such as acetone, methyl ethyl ketone; nitriles, such as acetonitrile; N,N-dialkylated amides, such as dimethyl formamide; also dimethyl sulphoxide and mixtures of these solvents with one another.

The process according to the invention is carried in the absence of water. A halogeno-acetanilide is obtained as intermediate product and which, after the solvent has been distilled off, can be reacted direct with the alkanol of the formula IV. This process step takes place in the presence of a hydrogen halide binding agent, i.e. an inorganic or organic base, for example alkali and alkaline earth metal hydroxides and carbonates; trialkylamines, such as trimethylamine, triethylamine, dialkyl anilines, pyridine and pyridine bases; alkali alkanolates of lower alkanols, such as sodium methylate, sodium ethylate, potassium ethylate etc. The reaction temperatures are between −20° C and +110° C; preferably they are between +10° C and 80° C.

The phenylazomethines of the formula III described as starting materials are known or they may be obtained by processes known in the art (cf. French Pat. No. 1,458,932) by reacting correspondingly alkylated anilines with formaldehyde.

The following Example will serve to illustrate the inventive process. The following Table lists further substituted halogeno-acetanilides of the formula I which have been manufactured by the described process.

EXAMPLE

While stirring, 27.8 of 2,6-diethyl-phenylazomethine in 30 ml of absolute diethyl ether are added at 10° C and within 1 hour to 19.8 g of chloracetyl chloride in 20 ml of absolute diethyl ether. In the process thereof the temperature rises to 30° C. Stirring is continued for 1 hour at room temperature, the solvent is removed and 34 g of 1-cyclopropyl ethanol are added. The reaction mixture is heated to 60° C and at this temperature 19.4 g of triethylamine in 20 ml of absolute benzene are added dropwise. A suspension forms which is further stirred for ¼ hour. Upon cooling, the mixture is treated with 200 ml of water and 200 ml of diethyl ether. The organic phase is again washed with water, dried over sodium sulphate and evaporated, to leave as residue 2,6-diethyl-N-(2-cyclopropylethoxy-methyl)-chloracetanilide in the form of a yellowish oil. It is purified over neutral aluminum oxide (activity level 1) using benzene is eluant.

Refractive index: $n_D{}^{20} = 1.5520$ (compound No. 1).
Analysis:
calc.: C 66,75; H 8,09; Cl 10,94 N 4,32;
found: C 66,92; H 8,16; Cl 10,34; N 4,29.
Further compounds of the formula V

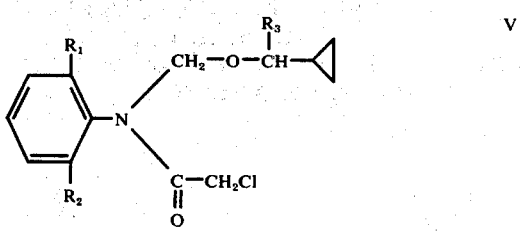

are manufactured according to the process described in the Example:

| Compound No. | $R_1$ | $R_2$ | $R_3$ | Physical Data |
|---|---|---|---|---|
| 2 | $CH_3$ | $C_2H_5$ | H | $n_D^{20} = 1{,}5264$ |
| 3 | $C_2H_5$ | $C_2H_5$ | H | $n_D^{20} = 1{,}5324$ |
| 4 | $CH_3$ | $C_2H_5$ | $CH_3$ | $n_D^{20} = 1{,}5258$ |
| 5 | $CH_3$ | i-$C_3H_7$ | H | $n_D^{20} = 1{,}5210$ |
| 6 | $CH_3$ | $CH_3$ | H | $n_D^{23} = 1{,}5113$ |
| 7 | $CH_3$ | i-$C_3H_7$ | $CH_3$ | $n_D^{20} = 1{,}5285$ |
| 8 | $CH_3$ | $CH_3$ | $CH_3$ | $n_D^{23} = 1{,}5155$ | also compounds of the formulae

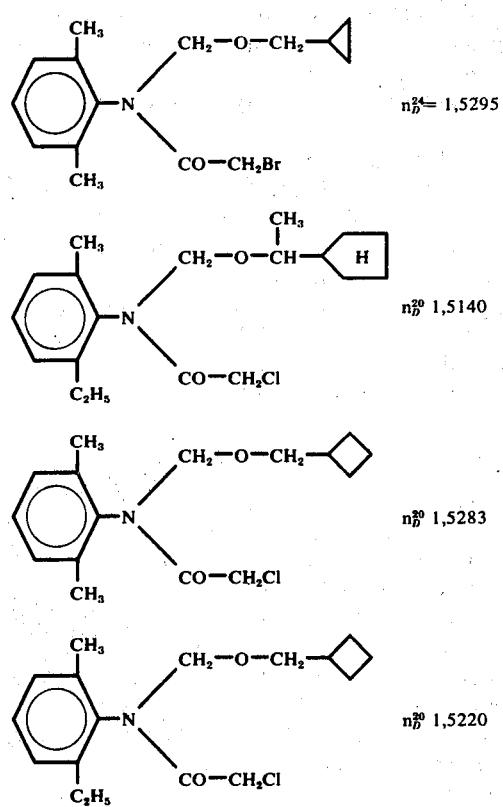

The active substances according to the invention display very good herbicideal properties against millet grass and similar weeds, e.g. Setaria sp. and Digitaria sp., against grasses such as Lolium sp. and also against certain dicotyledonous varieties of weed, e.g. Amaranthus sp., without detriment to sensitive cultivated plants such, for example, as beet, and hardy plants such as maize, cereals, soya beans, cotton, sorghum etc.

Furthermore, varieties of weeds which are difficult to combat in rice cultures (water and dry rice cultures) are attacked and destroyed by these active substances, e.g. Echinochloa sp. Since the active substances are non-toxic in conventional rates of concentration and have no deleterious effect on the balance of nature, they are very suitable for application in cultures of water rice. They may also be used for the important task of combating weeds in the areas surrounding the rice cultures, for example ditches, canal beds, embankments etc.

The active substances are applied preferably before germination of the plants (preemergence), but in some cases also after germination (postemergence). The rates of application are between 0.1 and 10 kg per hectare; but the weeds are readily brought under control or destroyed at rates of application as low as 0.5 kg per hectare.

Normally up to 10 kg of active substance per hectare are used to prevent weed infestation of railway embankments, factory grounds, roads etc.

Moreover, the active substances of the formula I also display growth repulating properties in that, for example, these delay the growth in height of gramineous grass and increase tillering. Weeds which seed strongly and rapidly are very sharply inhibited in their germination and emergence and thus removed from existing cultures of gramineous plants.

Preferred on account of their particular activity are halogeno-acetanilides of the formula Ia

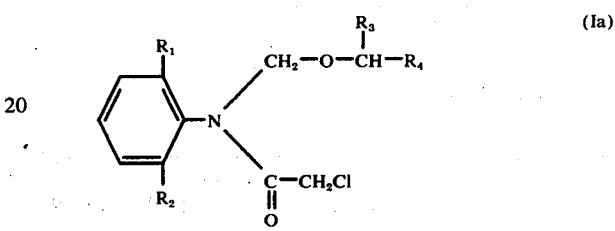

wherein $R_1$ represents methyl or ethyl, $R_2$ represents methyl, ethyl, isopropyl or sec. butyl, $R_3$ represents hydrogen or methyl and $R_4$ represents the cyclopropyl or cyclobutyl group. The compounds of the formula Ia, wherein $R_1$ represents the cyclopropyl group, possess particularly marked selective activity.

The herbicidal activity of the compounds according to the invention was determined by means of the following tests:

1. Herbicidal activity on application of the active substances before emergence of the plants Immediately after the test plants have been sown in a greenhouse, the active substances are applied to the surface of the soil in the form of an aqueous dispersion (obtained from a 25% wettable powder). The seed dishes are then kept at 22°–25° C and 50–70°% relative humidity. The test is evaluated after 28 days. 2,6-Diethyl-N-(methoxymethyl)-chloracetanilide (= compound A), known from U.S. Pat. No. 3,422,945, was used as comparative compound.

As test plants there were used:
cultivated plants:
wheat (Triticum)
maize (Zea mays)
soya beans (Glycine hyspida)
sugar beet (Beta vulgaris)
water rice (Oryza)
cotton (Gossypium)
weeds:
Digitaria sanguinalis
Setaria italica
Echinochloa crus galli
Sinapis alba
Amaranthus docendens The suspective rates of application used in this test are listed in the following Table. Evaluation was according to the following rating:
9 = plants undamaged (control)
1 = plants died off
2–8 = intermediate stages of damage
— = not tested

| Compound No. | Rate of application in kg/ha | Digitaria sanguinalis | Setaria italica | Echinochloa crus galli | Sinapis | Amaranthus | Oryza | Zea Mays | Glycine hyspida | Beta vulgaris | Gossypium | Triticum |
|---|---|---|---|---|---|---|---|---|---|---|---|---|
| 2 | 4 | 1 | 1 | 1 | 2 | 1 | 1 | 8 | 8 | 9 | — | 6 |
|   | 2 | 1 | 1 | 1 | 2 | 1 | 3 | 8 | 8 | 9 | — | 8 |
|   | 1 | 1 | 1 | 1 | 3 | 1 | 7 | 9 | 9 | 9 | 8 | 9 |
|   | 0,5 | 1 | 2 | 2 | 5 | 1 | 7 | 9 | 9 | 9 | 8 | 9 |
| 3 | 4 | 1 | 1 | 1 | — | 1 | 3 | 8 | 8 | 9 | 8 | 8 |
|   | 2 | 2 | 1 | 2 | — | 1 | 6 | 8 | 8 | 9 | 8 | 9 |
|   | 1 | 2 | 2 | 2 | — | 1 | 8 | 9 | 8 | 9 | 8 | 9 |
|   | 0,5 | 2 | 3 | 2 | — | 1 | 8 | 9 | 8 | 9 | 9 | 9 |
| 4 | 4 | 1 | 1 | 1 | — | 1 | — | 9 | 9 | 9 | 7 | 9 |
|   | 2 | 1 | 1 | 1 | — | 1 | 7 | 9 | 9 | 9 | 7 | 9 |
|   | 1 | 1 | 1 | 1 | — | 1 | 7 | 9 | 9 | 9 | 8 | 9 |
|   | 0,5 | 1 | 1 | 1 | — | 1 | 9 | 9 | 9 | 9 | 8 | 9 |
| 5 | 4 | 1 | 1 | 1 | — | 1 | — | 8 | 9 | 9 | 8 | — |
|   | 2 | 1 | 1 | 1 | — | 1 | — | 9 | 9 | 9 | 8 | 8 |
|   | 1 | 1 | 2 | 1 | — | 2 | — | 9 | 9 | 9 | 9 | 9 |
|   | 0,5 | 1 | 2 | 1 | — | 2 | — | 9 | 9 | 9 | 9 | 9 |
| 7 | 4 | 1 | 1 | 1 | — | 1 | 7 | 9 | 8 | 8 | 8 | 8 |
|   | 2 | 1 | 1 | 1 | — | 2 | 7 | 9 | 8 | 8 | 9 | 8 |
|   | 1 | 1 | 1 | 1 | — | 3 | 8 | 9 | 9 | 9 | 9 | 9 |
|   | 0,5 | 1 | 1 | 1 | — | 3 | 9 | 9 | 9 | 9 | 9 | 9 |
| A | 4 | 1 | 1 | 1 | 4 | 1 | 1 | 8 | 8 | 2 | 7 | 7 |
|   | 2 | 1 | 1 | 1 | 6 | 1 | 1 | 9 | 8 | 2 | 8 | 7 |
|   | 1 | 1 | 1 | 1 | 6 | 1 | 1 | 9 | 9 | 2 | 9 | 8 |
|   | 0,5 | 1 | 1 | 1 | 8 | 1 | 2 | 9 | 9 | 4 | 9 | 9 |

2. Preemergence test in rice in which weeds have been sown a. Dry test

In pots filled with garden soil are sown as test plant rice (Oryza Oryzoides) and as weed Echinochloa crus galli. The active substance is processed to a 25% wettable powder and is applied to the surface of the soil in the form of an aqueous dispersion immediately after the sowing (amount of broth: 100 ml/m²).

b. Wet test

The aqueous dispersion of the active substance is applied to the surface of the test pots and worked in to a depth of about 1 cm. Then the test plants (rice and Echinochloa crus galli) are sown and the soil is completely saturated with water. Upon emergence of the seed, the water level in the pots is brought to about 2–3 cm above the surface of the soil.

Both tests are carried out in a greenhouse at 24°–27° C and 70% relative humidity. The evaluation is carried out 28 days later according to the rating given in Test 1.

The comparative compounds used were compound A (of Test 1) and 2,6-diethyl-N-(n-butoxymethyl)-chloracetanilide (= compound B), known from U.S. Pat. No. 3,547,620. Compound B was tested in 5% granule formulation.

| Compound | Rate of application in kg/ha | Wet test | | Dry test | |
|---|---|---|---|---|---|
|   |   | Echinochloa crus galli | Rice | Echinochloa crus galli | Rice |
| 1 | 4 | 2 | 6 | 2 | 6 |
|   | 2 | 2 | 6 | 1 | 8 |
|   | 1 | 3 | 9 | 2 | 9 |
|   | 0,5 | 3 | 9 | 2 | 9 |
| 10 | 4 | 2 | 9 | 2 | 9 |
|   | 2 | 3 | 9 | 2 | 9 |
|   | 1 | 5 | 9 | 2 | 9 |
|   | 0,5 | 9 | 9 | 2 | 9 |
| A (known) | 4 | 1 | 1 | 1 | 1 |
|   | 2 | 1 | 1 | 1 | 1 |
|   | 1 | 1 | 1 | 1 | 3 |
|   | 0,5 | 2 | 2 | 1 | 4 |
| B (known) | 4 | 1 | 2 | 1 | 2 |
|   | 2 | 1 | 4 | 1 | 2 |
|   | 1 | 2 | 5 | 1 | 3 |
|   | 0,5 | 3 | 9 | 1 | 8 |

3. Herbicidal activity on preemergence application of the compound 2-methyl-6-ethyl-N-(cyclopropylmethoxymethyl)-chloroacetanilide (= compound 2) in maize cultures In a field test, maize was sown in the month of April on light soil in rows spaced 60 cm apart. The field was then divided up into plots of 4 m² in which about 60–80 maize plants per plot are to be expected.

One day after the sowing the plots were treated with the active substance concentration intended for them and obtained from an emulsion concentrate by dilution. Active substance A from Test 1 was used as comparative compound. The evaluation after 42 days referred to the state of the cultivated plant and to that of the naturally germinated weeds including the undesirable grasses. Damage to the plants is stated in the Table in percent, with the range of more servere damage being more differentiated than that of medium or slight damage. An activity very similar to that of compound No. 2 is attained with 2,6-dimethyl-N-(cyclopropylmethoxymethyl)-chloroacetanilide (= compound 6).

| Active Substance | Rate of application kg AS/ha | Maize | Echinochloa crus galli | Chenopodium album | Galinsoga parviflora | Galium aparine | Stellaria media | Mercurialis annua | Artiplex patulum |
|---|---|---|---|---|---|---|---|---|---|
| Compound 2 | 4 | 0% | 100% | 95% | 100% | 95% | 100% | 100% | 100% |
|  | 2 | 0% | 90% | 90% | 100% | 95% | 100% | 75% | 98% |
|  | 1 | 0% | 90% | 75% | 100% | 40–50% | 98% | 75% | 90% |
|  | 0,5 | 0% | 90% | 75% | 90% | 0–30% | 60% | 60% | 60% |
| Compound A | 4 | 2% | 90% | 40–50% | 100% | 0–30% | 100% | 40–50% | 100% |
|  | 2 | 2% | 90% | 40–50% | 90% | 0–30% | 85% | 40–50% | 100% |
|  | 1 | 0% | 40–50% | 40–50% | 75% | 0–30% | 60% | 40–50% | 85% |
|  | 0,5 | 0% | 0–30% | 0–30% | 40–50% | 0–30% | 40–50% | 0–30% | 0–30% |

The herbicidal agents are manufactured by mixing the active substances with suitable carriers and/or dispersing agents. In order to broaden the activity spectrum it is possible to add to those agents still other herbicides, for example from the series of the triazines, such as halogeno-diamino-s-triazines, alkoxy- and alkylthiodiamino-s-triazines, triazoles, diazines, such as uraciles, aliphatic carboxylic acids and halogenocarboxylic acids, halogenated benzoic acids and phenylacetic acids, aryloxyalkanecarboxylic acids, hydrazides, amides, nitriles, esters of such carboxylic acids, carbamic acids and thiocarbamic acids, urea etc.

The agents according to the invention are manufactured in known manner by intimately mixing and/or grinding active substances of the formula I with the suitable carriers, optionally with the addition of dispersants or solvents which are inert towards the active substances. The active substances may be available and can be used in the following forms:

Solid forms
  dusts, tracking agents, granules, coated granules, impregnated granules and homogeneous granules.

Liquid forms:
  a. active substances which are dispersible in water: wettable powders, pastes, emulsions;
  b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, prepicipated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

The particle size of the carriers for dusts is advantageously up to about 0.1 mm, for tracking agents from about 0.075 to 0.2 mm, and for granules 0.2 mm or larger.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of mono-alkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance. i.e. wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehye, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium salt of oleoyl methyl tauride, diertiary acetalene glycols, dialkyl dilauryl ammonium chloride and fatty acid alkali and alkaline earth metal salts.

Suitable anti-foam agents are silicones.

The active substances are so mixed, ground sieved and strained with the additives mentioned above that, in wettable powders, the solid particle size of from 0.02 to 0.04 and in pastes, of 0.03 is not exceeded. To produce emulsifiable concentrates and pastes, dispersing agents such as those given in the previous paragraphs, organic solvents and water are used. Examples of suitable solvents are the following: alcohols, benzene, xylenes, toluene, dimethyl sulfoxide, and mineral oil fractions boiling between 120° and 350° C. The solvents must be practically odorless, not phytotoxic, inert to the active substances and not readily inflammable.

Furthermore, the agents according to the invention can be applied in the form of solutions. For this purpose the active austances or several active substances of general formula II are dissolved in suitable organic solvents, mixtures of solvents or in water. Aliphatic and aromatic hydrocarbons, chlorinated derivatives thereof, alkyl naphthalenes and mineral oils alone or mixed with each other, can be used as organic solvents.

In addition to fungicidal active substances, the agents described according to the invention can be mixed with other biocidally active substances or agents. Thus in order to broaden the activity spectrum the new agents may contain, for example, insecticides, fungicides, bactericides, fungistatics, bacteriostatics or nematocides, in addition to the cited compounds of the formula I. The agents according to the invention may also contain plant fertilisers, trace elements etc.

The active substances of the formula I can, for example, be formulated as follows. The parts denote parts by weight.

Granules

The following substances are used to manufacture 5% granules:
5 parts of 2-methyl-6-ethyl-N-(cyclopropylmethoxymethyl)-chloracetanilide,
0.25 parts of epichlorohydrin,
0.25 parts of cethyl polyglycol ether,
3.50 parts of polyethylene glycol ether,
91 parts of kaolin (particle size: 0.3–0.8 mm).

The active substance is mixed with epichlorohydrin and the mixture dissolved in 6 parts of acetone, then polyethylene glycol ether and cetyl polyglycol ether are added. The resulting solution is sprayed on kaolin and then evaporated in vacuo.

Wettable Powder

The following constituents are used to manufacture (a) a 70%, (b) a 25% and (c) a 10% wettable powder:
a.
70 parts of 2-methyl-6-ethyl-N-(cyclopropylmethoxymethyl)-chloracetanilide,
5 parts of sodium dibutylnaphthalene sulphonate,
3 parts of naphthalenesulphonic acid/phenolsulphonic acid/formaldehyde condensate (3:2:1),
20 parts of kaolin,
22 parts of Champagne chalk;
b.
25 parts of 2,6-diethyl-N-(cyclopropylmethoxymethyl)-chloracetanilide,
5 parts of sodium oleylmethyltauride,
2.5 parts of napthalenesulphonic acid/formaldehyde condensate,
0.5 parts of carboxymethyl cellulose,
5 parts of neutral potassium aluminium silicate,
62 parts of kaolin;
c.
10 parts of 2-methyl-6-ethyl-N-(1-cyclopropylethoxymethyl)-chloracetanilide,
3 parts of a mixture of the sodium salts of saturated fatty alcohol sulphates,
5 parts of napthalenesulphonic acid/formaldehyde condensate,
82 parts of kaolin.

The indicated active substance is applied to the corresponding carriers (kaolin and chalk) and then these are mixed and ground, to yield wettable powders of excellent wettability and having an excellent capacity for forming suspensions. By diluting these wettable powders with water it is possible to obtain suspensions of every desired concentration of active substance. Such suspensions are used for combating weeds in crops of cultivated plants.

Paste

The following substances are used to manufacture a 45% paste:
45 parts of 2,6-diethyl-N-(1-cyclopropylethoxymethyl)-chloracetanilide,
5 parts of sodium aluminium silicate,
14 parts of cetyl polyglycol ether with 8 mols of ethylene oxide,
1 part of oleyl polyglycol ether with 5 mols of ethylene oxide,
2 parts of spindle oil,
10 parts of poyethylene glycol,
23 parts of water.

The active substance is intimately mixed with the addition in appropriate devices and ground. A paste is obtained from which, by diluting it with water, is possible to manufacture suspensions of every desired concentration of active substance.

Emulsion Concentrate

To manufacture a 25% emulsion concentrate
25 parts of 2-methyl-6-ethyl-N-(1-cyclopropylethoxymethyl)-chloranilide,
5 parts of a mixture of nonylphenolpolyoxyethoxyyethylene and calcium, dodecylenesulphonate,
35 parts of 3,5,5-trimethyl-2-cyclohexen-1-one,
35 parts of dimethyl formamide,
are mixed together. This concentrate can be diluted with water to give emulsions in desired concentrations. Such emulsions are suitable for combating weeds in crops of cultivated plants, e.g. maize, rice, sugar beet etc.

We claim:
1. A compound of the formula I

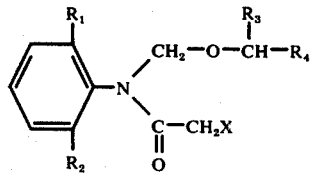

wherein $R_1$ and $R_2$ each independently represents hydrogen or lower alkyl containing from 1 to 4 carbon atoms, $R_3$ represents hydrogen or the methyl group, $R_4$ represents cycloalkyl containing from 3 to 5 carbon atoms, and X represents chlorine or bromine.

2. A compound according to claim 1 of the formula Ia

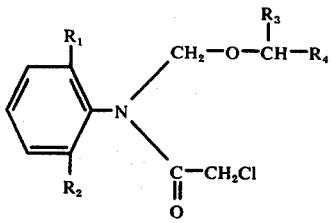

wherein $R_1$ represents methyl or ethyl, $R_2$ represents methyl, ethyl, isopropyl or sec.butyl, $R_3$ represents hydrogen or methyl, and $R_4$ represents the cyclopropyl or cyclobutyl group.

3. A compound according to claim 1 of the formula V

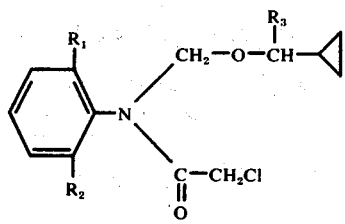

wherein $R_1$ represents methyl or ethyl, $R_2$ represents methyl, ethyl, isopropyl or sec. butyl, and $R_3$ represents hydrogen or methyl.

4. 2-methyl-6-ethyl-N-(cyclopropylmethoxymethyl)-chloracetanilide according to claim 1.

5. 2,6-diethyl-N-(cyclopropylmethoxy-methyl)-chloracetanilide according to claim 1.

6. 2-methyl-6-ethyl-N-(1-cyclopropylethoxymethyl)-chloracetanilide according to claim 1.

7. 2,6-diethyl-N-(1-cyclopropylethoxymethyl)-chloracetanilide according to claim 1.

8. 2-methyl-6-isopropyl-N-(cyclopropylmethoxymethyl)-chloracetanilide according to claim 1.

9. 2-methyl-6-isopropyl-N-(1-cyclopropylethoxymethyl)-chloracetanilide according to claim 1.

10. 2-methyl-6-ethyl-N-(1-cyclopentylethoxymethyl)-chloracetanilide according to claim 1.

11. 2,6-dimethyl-N-(cyclopropylmethoxy-methyl)-chloracetanilide according to claim 1.

12. 2,6-dimethyl-N-(cyclobutylmethoxy-methyl)-chloracetanilide according to claim 1.

* * * * *